United States Patent
Suzuki

(10) Patent No.: US 7,935,861 B2
(45) Date of Patent: May 3, 2011

(54) LIQUID DISTRIBUTION UNIT AND ABSORBENT PRODUCT HAVING THE SAME

(75) Inventor: Migaku Suzuki, Tokyo (JP)

(73) Assignee: Japan Absorbent Technology Institute, Tokyo (JP)

( * ) Notice: Subject to any disclaimer, the term of this patent is extended or adjusted under 35 U.S.C. 154(b) by 510 days.

(21) Appl. No.: 10/468,373

(22) PCT Filed: Feb. 19, 2002

(86) PCT No.: PCT/JP02/01419
§ 371 (c)(1),
(2), (4) Date: Aug. 19, 2003

(87) PCT Pub. No.: WO02/065965
PCT Pub. Date: Aug. 29, 2002

(65) Prior Publication Data
US 2004/0087927 A1    May 6, 2004

(30) Foreign Application Priority Data
Feb. 20, 2001   (JP) .................................. 2001-043494

(51) Int. Cl.
*A61F 13/15*   (2006.01)
(52) U.S. Cl. .................. 604/378; 604/385.101
(58) Field of Classification Search .......... 604/378–384, 604/385.101
See application file for complete search history.

(56) References Cited

U.S. PATENT DOCUMENTS

| | | | | |
|---|---|---|---|---|
| RE26,151 | E | * | 1/1967 | Duncan et al. ................ 604/375 |
| 3,929,135 | A | * | 12/1975 | Thompson ............... 604/385.08 |
| 4,323,069 | A | * | 4/1982 | Ahr et al. ....................... 604/378 |
| 4,341,217 | A | * | 7/1982 | Ferguson et al. ........ 604/385.08 |
| 4,535,020 | A | * | 8/1985 | Thomas et al. ............... 428/131 |
| 4,592,751 | A | | 6/1986 | Gegelys |
| 4,710,185 | A | * | 12/1987 | Sneyd et al. .................. 604/372 |
| 4,908,026 | A | * | 3/1990 | Sukiennik et al. ............ 604/378 |
| 5,009,653 | A | * | 4/1991 | Osborn, III ............. 604/385.04 |

(Continued)

FOREIGN PATENT DOCUMENTS

JP    5-7221    2/1993

(Continued)

OTHER PUBLICATIONS

Merriam-Webster OnLine definition of "space".*

*Primary Examiner* — Tatyana Zalukaeva
*Assistant Examiner* — Benedict L Hanrahan
(74) *Attorney, Agent, or Firm* — Frommer Lawrence & Haug LLP; Ronald R. Santucci

(57) ABSTRACT

A liquid distribution unit disposed in a position between an absorbent member and a wearer's body. The liquid distribution unit includes a sheet, the sheet including a plurality of openings defined through material which is otherwise liquid impermeable, and a plurality of introductory tubes extending toward the absorbent member, and each one of the introductory tubes includes one first end and one second end. Each first end of the tubes is connected to the sheet so that a center of each of a plurality of openings of the sheet is coincident with a center of an opening of each first end. The introductory tubes are adjacent to one another through an empty space. An absorbent product having the distribution unit is provided.

15 Claims, 9 Drawing Sheets

U.S. PATENT DOCUMENTS

| | | | |
|---|---|---|---|
| 5,019,062 A * | 5/1991 | Ryan et al. | 604/359 |
| 5,078,710 A * | 1/1992 | Suda et al. | 604/383 |
| 5,366,782 A * | 11/1994 | Curro et al. | 428/137 |
| 5,387,209 A * | 2/1995 | Yamamoto et al. | 604/384 |
| 5,401,267 A * | 3/1995 | Couture-Dorschner et al. | 604/384 |
| 5,415,640 A * | 5/1995 | Kirby et al. | 604/383 |
| 5,545,155 A * | 8/1996 | Hseih et al. | 604/378 |
| 5,635,275 A * | 6/1997 | Biagioli et al. | 428/132 |
| 5,716,351 A | 2/1998 | Roe et al. | |
| 5,961,505 A * | 10/1999 | Coe et al. | 604/378 |
| 6,103,953 A * | 8/2000 | Cree et al. | 604/365 |
| 6,117,523 A * | 9/2000 | Sugahara | 428/134 |
| 6,242,074 B1 * | 6/2001 | Thomas | 428/137 |
| 6,417,426 B1 * | 7/2002 | Takai et al. | 604/378 |
| 6,610,904 B1 * | 8/2003 | Thomas et al. | 604/383 |
| 6,849,319 B2 * | 2/2005 | Cree et al. | 428/138 |
| 2003/0097113 A1 * | 5/2003 | Molee | 604/385.101 |

FOREIGN PATENT DOCUMENTS

| | | |
|---|---|---|
| JP | 5-38350 A | 2/1993 |
| JP | 5-237149 A | 9/1993 |
| JP | 7-502433 A | 3/1995 |
| JP | 9-299402 A | 11/1997 |
| JP | 2000-201975 A | 7/2000 |
| JP | 2000-232985 A | 8/2000 |
| WO | WO 93/11726 | 6/1993 |

\* cited by examiner

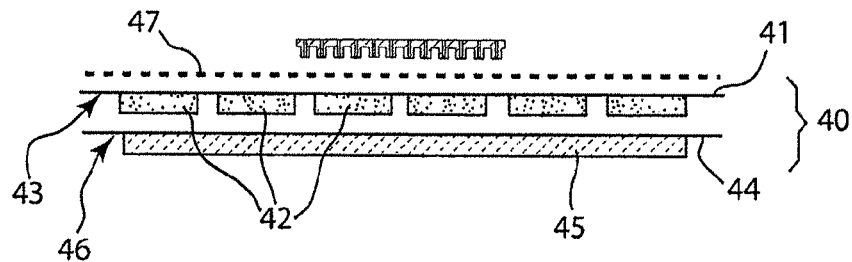
Fig. 9
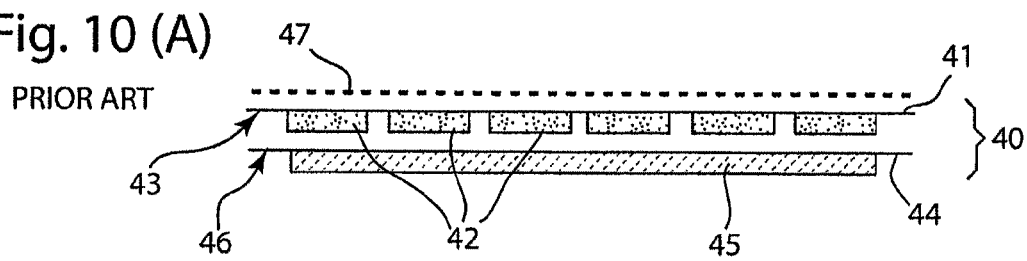
Fig. 10 (A) PRIOR ART
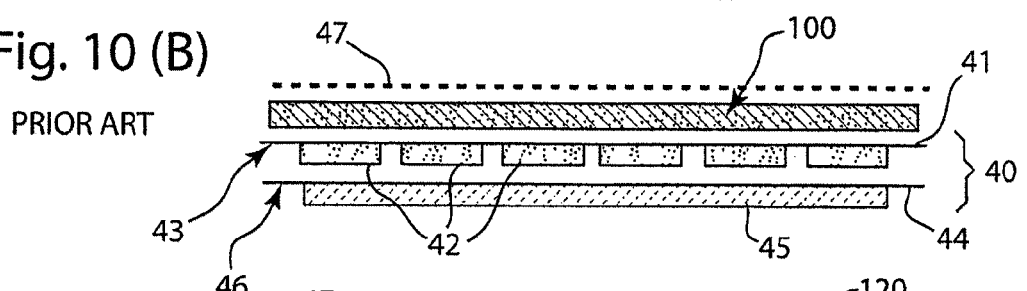
Fig. 10 (B) PRIOR ART
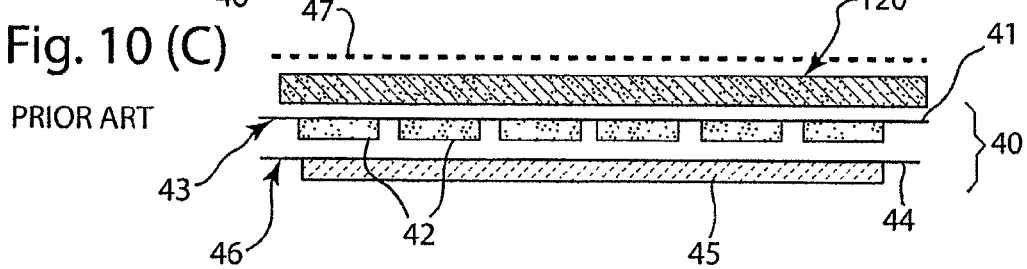
Fig. 10 (C) PRIOR ART

LIQUID DISTRIBUTION UNIT AND ABSORBENT PRODUCT HAVING THE SAME

This application is a 371 of PCT/JP02/01419 filed on Feb. 19, 2002, published on Aug. 29, 2002 under publication number WO 02/065965 A1 and claims priority benefits of Japanese Patent Application No. 2001-43494 filed Feb. 20, 2001.

TECHNICAL FIELD

The present invention relates to a liquid distribution unit which is applied to absorbent articles such as diapers for infants and adults, sanitary items for women, and medical blood absorbents in order to improve capabilities of the absorbents. The present invention also relates to a method of manufacturing the liquid distribution unit.

BACKGROUND ART

Absorbent articles for broad use in general have been developed mainly for use in disposal of urine. These absorbent articles have been desired to be capable of handling changes caused by various factors such as a wearer's posture, intake condition of water, and physical condition, for example, wearing posture and changes of discharge states such as amount, quality and speed of discharged urine. To securely deal with these changes, an area and a volume sufficiently larger than necessary on usual use conditions need to be imparted to the absorbent articles. On the other hand, from a viewpoint of a wearer's comfort, the absorbent articles are preferably thinner and compacter.

Considering from an aspect of absorption efficiency, the absorbent articles, which have margins in this manner, have an absorbent with a remarkably bad efficiency, and are also undesirable from a viewpoint of the wearer's comfort. In order to improve area and volume efficiencies of the absorbent articles, it is important to form the absorbent itself to be as thin and compact as possible, and further to control the flow of discharged liquid. That is, a mechanism needs to be disposed in which the discharged liquid is guided to an intended/desired position of the absorbent and the discharged liquid is uniformly distributed over the whole surface of the absorbent. The absorbent of one of the absorbent articles cannot be formed to be thinner or compacter until these considerations are made, and there has been a demand for development of the absorbent articles which have these capabilities.

There have been a large number of proposals concerning the reduction of the size of the absorbent. For example, in Japanese Patent No. 3,090,266, there is disclosed an absorbent sheet containing three components including: an absorption layer mainly comprising super absorbent polymer particles; a nonwoven fabric substrate for supporting the super absorbent polymer particles; and a binder component for bonding the super absorbent polymer particles to one another and for bonding the super absorbent polymer particles to the nonwoven fabric substrate. The nonwoven fabric substrate is constituted of a nonwoven fabric which has a multilayered structure including a diffusion layer (P) formed of a fiber layer relatively high in hydrophilicity and high in density and an acquisition layer (Q) relatively low in hydrophilicity and low in density. On the surface of the absorbent sheet, an absorption region phase (phase A) including the absorption layer and the nonwoven fabric substrate carrying the absorption layer, and a diffusion/acquisition region phase (phase B) in which the super absorbent polymer particles hardly exist and which is mainly formed of only the non-woven substrate are distributed so that the phases can be distinguished from each other.

Moreover, in Japanese Patent Application Laid-Open No. 2000-232,985, there is described a disposable incontinence liner in which an absorption sheet is disposed between a top sheet and back sheet. For the absorption sheet, there is described an absorbent sheet including: an absorption layer in which polymeric absorbent particles are bonded by microfibrillated fine fibers; and a sheet support material for supporting this absorption layer. The polymeric absorbent particles having specific weights, and the absorbent sheet having specific thickness and rigidity/softness are used.

Further in Japanese Patent No. 2,872,851, there is disclosed an absorbent article including a surface material having permeability to liquid, an absorbent having liquid holding property, and a leak preventive material having impermeability to the liquid. A part or all of the absorbent is constituted of an absorption sheet in which polymeric absorbent particles are fixed to an absorption material by an adhesive applied in a dot, linear, or curve form. For the adhesive, a 180° peeling adhesive force (JIS C2107) is not less than 500 g and not more than 4000 g. An occupying area of the applied adhesive is not less than 10% and not more than 70%.

Moreover, an absorbent sheet in which polymeric absorbent particles are mixed in high concentration in a so-called airlaid method of molding a pulp sheet by a dry process and bonded/integrated by a heat-melting binder also starts to be used in an ultrathin absorbent article.

However, although the absorbent article using the above-described absorbent sheet is thin and compact as compared with the conventional article, further improvement is still necessary with respect to the efficiency.

Additionally, as a measure for efficiently absorbing the discharged liquid into the thin absorbent, a bulky nonwoven fabric has heretofore been added as a diffusion sheet, distribution sheet, transfer sheet, or acquisition sheet to the surface of the thin absorbent. These common ideas are based on the use of the diffusion phenomenon of the liquid using capillaries among the constituting fibers. An attempt has also been made to dispose a foam or bulky opening film subjected to a surface hydrophilic treatment for temporarily trapping the liquid between a top sheet and the absorbent or in the absorbent.

The present invention has been derived from an attempt to purely incorporate a mechanical liquid distribution mechanism which is disposed in contact with a discharge port of body fluid into the absorbent article.

DISCLOSURE OF THE INVENTION

An object of the present invention is to provide a distribution unit capable of distributing a liquid discharged from a wearer into the surface of an absorbent.

According to one aspect of the present invention, there is provided a liquid distribution unit disposed to keep in contact with the surface of a liquid permeable sheet of an absorbent article disposed in a contact position with respect to a wearer on the wearer's side.

The liquid distribution unit includes a plurality of liquid distribution passages in a hanging direction with respect to the surface of the unit, and the liquid distribution unit divides and branches finely the liquid supplied to the surface of the unit along the surface of the surface sheet.

The liquid distribution unit may include a plurality of openings, and introductory tubes extending toward the surface of an absorbent member from the openings, and may be formed so as to guide the liquid from the openings toward the surface of the absorbent member through the introductory tubes.

For each opening, preferably, when its opening surface is approximated to an ellipse, its short axis is at least 0.5 mm, its long axis is 10 mm at maximum, its open area ratio is not less than 10% and not more than 90%. The number of openings is preferably at least 200 openings per 100 cm$^2$.

The length of the introductory tube is preferably not less than 0.50 mm and not more than 5 mm.

The introductory tube forming a funnel shape, which has a large inlet diameter on its opening surface side and a small outlet diameter, is advantageous.

The liquid distribution unit can be constituted of a thermoplastic film having a thickness which is not less than 10 μm and not more than 100 μm.

For the liquid distribution unit, wettability may also be improved by treatment of the surface of the unit with a hydrophilic agent, and mobility of the liquid from the opening is improved in this case.

Moreover, the absorbent member includes a plurality of absorbent sheets laminated upon one another, and the liquid distribution unit may include a portion exposed onto the absorbent sheet positioned in a top layer, and a portion extending to reach the absorbent sheet positioned in a lower layer of the absorbent sheet of the top layer.

According to the present invention, there is further provided an absorbent article including the above-described liquid distribution unit. In this case, the absorbent article includes a liquid permeable surface sheet positioned on an inner side with respect to a wearer's body in a wearing state; a liquid impermeable sheet positioned on an outer side from the surface sheet; and an absorbent member containing super absorbent polymer particles as a major component disposed between the surface sheet and the liquid impermeable sheet. The liquid distribution unit is disposed between the body surface of the wearer and the absorbent member.

The absorbent member for use preferably contains at least 50% by weight or more of the super absorbent polymer particles.

A liquid permeable nonwoven fabric may further be disposed on the liquid distribution unit.

A ratio of an area occupied by the liquid distribution unit with respect to the total area of the surface sheet is preferably not less than 5% and not more than 50%, and the unit is partially disposed so as to have an area of at least 10 cm$^2$.

The liquid permeable nonwoven fabric may further be disposed only on the partially disposed liquid distribution unit.

Furthermore, an acquisition layer or diffusion layer may be disposed under the liquid distribution unit. In order to broadly distribute and diffuse the liquid in a surface part, a liquid impermeable sheet is sometimes disposed in the lower surface of the liquid distribution unit to partially block an outlet of the distribution unit.

The absorbent member constituted of the absorbent sheet including a nonwoven substrate, super absorbent polymer particles, and microfibrillated cellulose can be used.

Alternatively, the absorbent member may also be constituted of the absorbent sheet including a wood pulp obtained by a so-called air-laid method, super absorbent polymer particles, and bonding material.

The absorbent member has a retained absorption amount of 300 cc or more. When a water absorption speed is measured every 100 cc at an interval of ten minutes three times, the water absorption speed is 60 sec or less in any measurement, and a deviation among the three measurement data is suitably 30 sec or less.

Furthermore, the absorbent sheet has a bent shape whose transverse section has a Z-shape, the liquid distribution unit is disposed only in a center portion of the upper surface of the absorbent sheet, and the unit can be used in this mode.

BRIEF DESCRIPTION OF THE DRAWINGS

FIG. 9 is a vertical sectional view schematically showing an absorbent part of an absorbent article according to the present invention including the liquid distribution unit;

FIGS. 10 (A) to 10(C) show vertical sectional views schematically showing the absorbent parts of different conventional absorbent articles;

FIGS. 13(A) to 13 (D) show plan views showing different bonding modes of a bonding portion for bonding the liquid distribution unit of the present invention with respect to the absorbent member;

BEST MODE FOR CARRYING OUT THE INVENTION

A liquid distribution unit of the present invention will be described hereinafter in detail with reference to the drawings.

Figure 1:
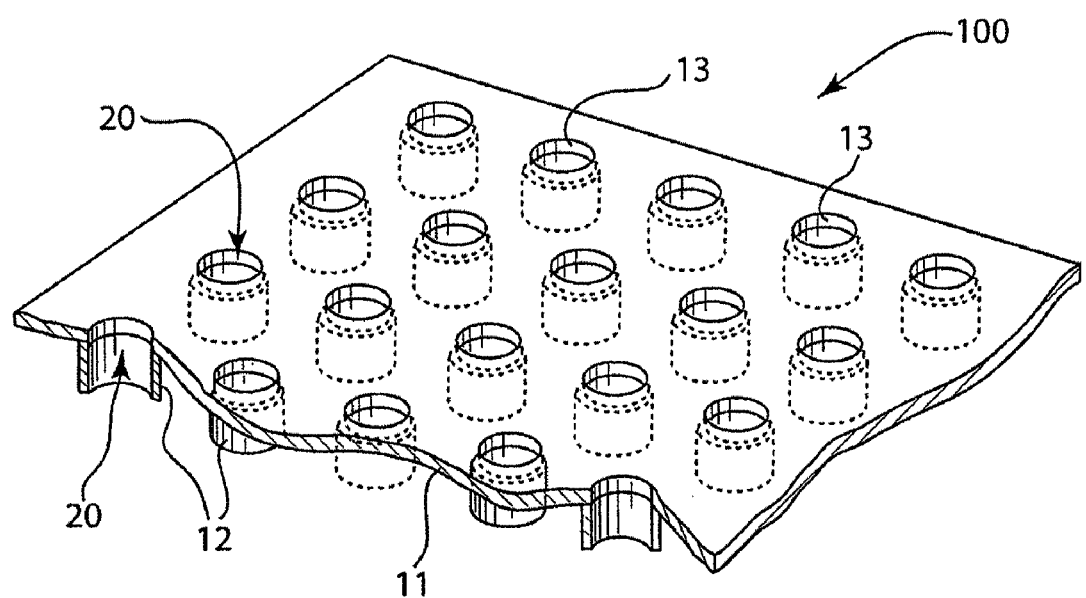
FIG. 1 is a perspective view showing a cut part of a liquid distribution unit according to one embodiment of the present invention.

FIG. 1 is a model diagram showing one example of the liquid distribution unit according to the present invention. A liquid distribution unit 100 includes a sheet 11 of liquid impermeable material having a large number of openings, and a large number of tubular introductory tubes 12 extending in a direction hanging from the surface of the sheet 11. To simplify the description, in FIG. 1, a large number of circular openings 13 are formed in the sheet 11 of liquid impermeable material. The introductory tube 12 having an inner diameter substantially equal to a diameter of the opening 13 is disposed so that an axial center of the introductory tube 12 agrees with a center of the opening 13. In the corresponding position, the tube is connected to the lower surface of the liquid sheet 11 of liquid impermeable material. This opening 13 and a center hole of the introductory tube 12 form a liquid distribution passage 20.

Figure 2:
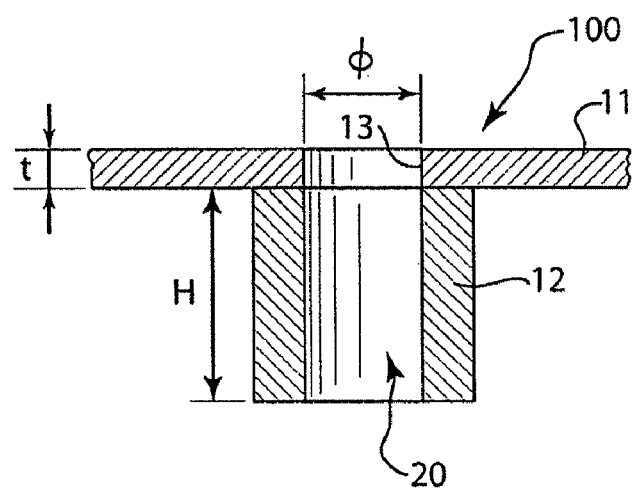
FIG. 2 is a vertical sectional view of a part of the liquid distribution unit shown in FIG. 1.

FIG. 2 shows an enlarged sectional view of a part of the liquid distribution unit 100 shown in FIG. 1. In the figure, the thickness of the sheet 11 of liquid impermeable material is shown by t, the diameter of the opening 13 is shown by Φ, and the length of the introductory tube 12 is shown by H.

A mechanism for distributing the liquid in the liquid distribution unit of the present invention will be described hereinafter.

Figure 3:
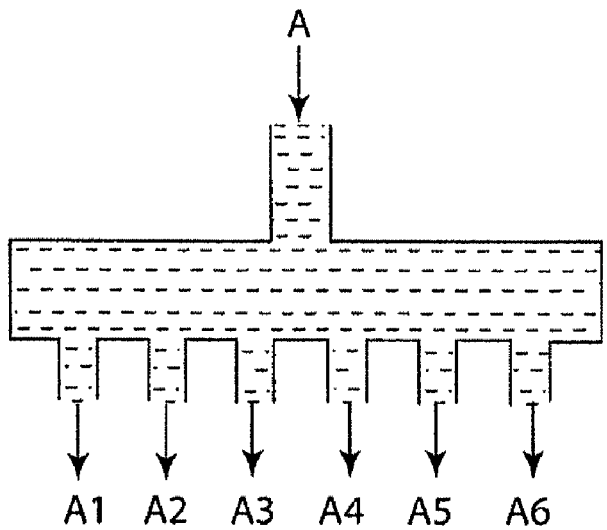
FIG. 3 is an explanatory view showing the principles of liquid distribution in the liquid distribution unit of the present invention.

In the present invention, as shown in FIG. 3, the term of "the distribution of the liquid" means a phenomenon in which a flow A of the liquid which has entered via an upper inlet is discharged as a plurality of mechanically divided flows A1, A2, A3, . . . An in going out of lower outlets.

Figure 4:
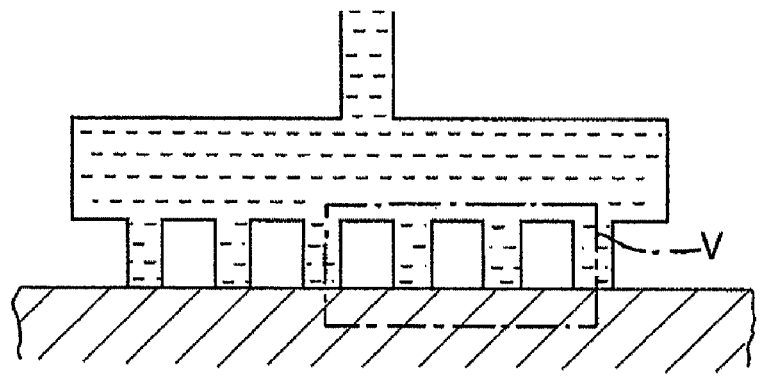
FIG. 4 is an explanatory view showing a mechanism of liquid distribution occurring between the liquid distribution unit of the present invention and an absorbent disposed under the unit.
Figure 5:
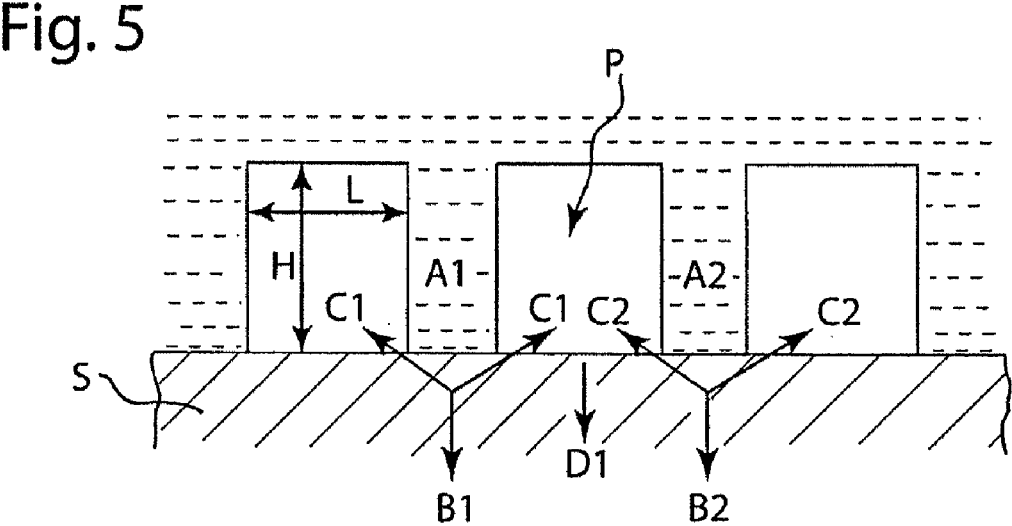
FIG. 5 is an enlarged view of a part shown by V of FIG. 4.

As shown in FIG. 4 and FIG. 5 showing a part of FIG. 4 in an enlarged size, when the divided flows A1 to An collide with the surface of an absorbent S, the flows are further divided into flows B1 and B2 . . . Bn absorbed by the absorbent S and flows C1, C2 . . . Cn overflowing to spaces P along the surface in accordance with flow amount and speed. The flow which overflows in the space P having a height H and width L formed in the liquid distribution unit 100 and the surface of the absorbent S is absorbed into the absorbent S with a flow shown by D1.

In this manner, the flow A is formed into the divided flows A1, A2 . . . An, and is further multi-divided into B1, B2 . . . Bn, C1, C2 . . . Cn, and D1, D2 . . . Dn, and the finely divided flows are supplied into the absorbent S. As a result, the irregularly discharged liquid is formed into the controlled fine flow by a mechanical distribution effect, and rapidly spreads over the surface of the absorbent by the distribution effect. Only a part of the absorbent S is prevented from locally swelling, and it is possible to effectively use the whole surface of the absorbent S. To impart such a uniform surface diffusion effect is especially important for the absorbent containing super absorbent polymer (SAP) particles at a high ratio, which has characteristics that the thickness is small and capacity is large but absorption speed is low.

As clear from the above description, the following basic conditions are necessary for the liquid distribution unit of the present invention to fulfill the desired functions.

(1) To distribute the liquid, the distribution unit needs to have an ability to retain a certain liquid amount. For this, it is important to dispose a space having a height H and width L in an appropriate size in FIG. 5 between the liquid distribution unit and the surface of the surface sheet positioned under the unit.

(2) It is necessary to have an introduction function of moving the liquid from the opening to introduce the liquid into the absorbent surface.

(3) An isolating distance (corresponding to the length H of the introductory tube) for isolating the opening from the surface sheet is required.

(4) A space (P) needs to exist between the introductory tubes disposed adjacent to one another. For the space, in a structure in which there is not any introductory tube, for example, in a structure in which the opening is disposed in a thick sheet, this space is not generated, and therefore the function aimed of the present invention is not obtained. When the introductory tube becomes thinner and has a longer length (H), the space becomes larger.

(5) To maintain stability of the shape, that is, to obtain characteristics that the liquid distribution unit is not deformed or collapsed even under loads such as a wearer's weight, it is important that the sheet of liquid impermeable material having a large number of openings for use in the liquid distribution unit has a certain degree of thickness. The thickness also depends on the material which constitutes the liquid impermeable sheet. However, it is desirable to have a thickness of at least 10 μm or more, more preferably 20 μm or more.

This will be described with reference to FIG. 2. When the transverse sectional shape of the introductory tube 12 is circular, the diameter Φ indicates a value of 0.5 mm or more, preferably 1 mm to 10 mm, the length H is 0.5 mm or more, preferably 1 mm to 10 mm, and the thickness t of the sheet of liquid impermeable material having a large number of openings is 10 μm or more, preferably 20 μm to 200 μm.

As the material constituting the liquid distribution unit, the material having an absorbing property entirely like the nonwoven fabric which has heretofore been used as an acquisition layer or diffusion layer is not therefore used in the liquid distribution unit according to the present invention because the material itself absorbs the liquid. The material itself may be impermeable to the liquid so that the liquid is retained as little as possible. On the other hand, a metal plate is satisfactory both in shape stability and distribution effect, but is excessively high in rigidity, and it is difficult to apply the metal plate to the absorbent article. The appropriate material, for example, is a thermoplastic film or a bonded material of the film with the nonwoven fabric. Examples of the material include: a single-layer film of a simple substance or a blend material of a thermoplastic synthetic resin such as PE, PP, PET, EVA, MA, MMA; a co-extrusion film such as PE/PP, PE/PET, low melting point PET/PET, and EVA/PE; and a bonded material of the single-layer film, co-extrusion film, and nonwoven fabric such as a spun bond nonwoven fabric, thermal bond nonwoven fabric, and tissue. The thickness of the film is 10 μm or more, and preferably 100 μm or less, because a problem occurs in moldability of the opening with an excessively large thickness. It is to be noted that in order to reduce the liquid remaining in the surface locally, a surface hydrophilic treatment is permitted for improvement of surface wettability, and is sometimes rather desirable to facilitate the movement of the liquid from the opening. For the hydrophilic agent, measures are taken such as the coating with an anionic, cationic, or nonionic surfactant and the mixing of the hydrophilic components such as PEG in a material polymer itself to impart hydrophilicity.

In order to industrially produce such a structure, for example, any of the following methods would preferably be used.

(1) A method of using a metal mold to extrude plastic resin directly from a molding machine and molding the distribution unit. In this method, it is necessary to form a smooth and flexible molded material without any protrusion or surface damage.

(2) A method of forming a concave/convex portion in a net formed of plastic filaments having a certain degree of rigidity by thermoforming. In this thermo-formed material, the concave portion functions as the opening, and the convex portion functions as the introductory tube. In this case, the net needs to have a mesh size to such a degree that the liquid can sufficiently pass through the net. For example, the size is preferably 40 meshes to 100 meshes.

(3) A method of forming a deep dent in a liquid impermeable plastic film by thermoforming and opening the bottom of the dent mechanically or further by a heat treatment.

(4) A method of forming a deep embossed groove in a plastic film and heating and vertically/laterally drawing the film to produce an opening in the bottom of the groove.

(5) A method of guiding a plastic film in a heated state into a porous surface cylinder whose inner pressure is reduced, applying heat air to the film to suck the film, and forming an opening in accordance with the pore size of the cylinder to obtain a molded material to which the introductory tube is also formed in accordance with the thickness of the porous cylinder.

Figure 6:
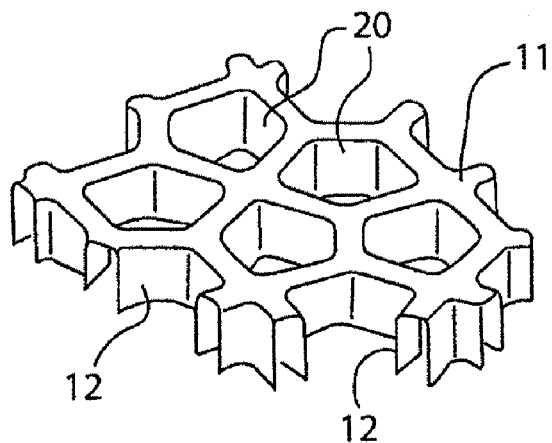
FIG. 6 is a perspective view showing a part of the liquid distribution unit according to another embodiment of the present invention.

The shape of the opening and arrangement example of the liquid distribution unit obtained in the above method (4) or (5) are shown in FIG. 6.

In order to effectively perform the fine division of the liquid, it is important to appropriately control the state of the opening which is the inlet of the liquid.

The opening state is represented by the opening shape, the number of openings, opening ratio (open area ratio), and the like.

The opening shape may be any of circular, elliptic, square, rectangular, quadrangular, and hexagonal shapes. However, when the size of the opening is excessively small, the movement efficiency of the liquid is bad. Conversely, when the size is excessively large, a liquid division effect worsens.

When the opening shape is approximated to an elliptic shape and its short axis is less than 0.5 mm, surface tension acts, and the passage of the liquid is inhibited. A preferable short axis size is not less than 0.5 mm. On the other hand, when the size is excessively large, a passing property of the liquid becomes satisfactory, but the division effect worsens, and therefore the long axis size is 10 mm at maximum, preferably 5 mm.

The number of openings also largely influences the division effect. When the number of openings per unit area is small, it is necessary to have a large opening area of each opening, and the division efficiency worsens for the above-described reason. Therefore, the number of openings is at least 200 per 100 $cm^2$, preferably at least 500 per 100 $cm^2$.

The area of openings represents an open area ratio at a time when the total area of the distribution unit is assumed to be 100. Zero % indicates that there is not any opening. The open area ratio is preferably 10% or more, more preferably 90% or less. When the open area ratio is less than 10%, the movement speed of the liquid is excessively low. When the open area ratio exceeds 90%, the shape stability of the liquid distribution unit becomes worse, and so the open area ratio is preferably in a range of 20% to 80%.

In the above description, there is also a cylindrical introductory tube having a circular transverse section, but in the present invention, an introductory tube having a shape other than the cylindrical shape can be applied. Some examples are shown in FIGS. 7(A), 7(B), 7(C).

Figure 7:
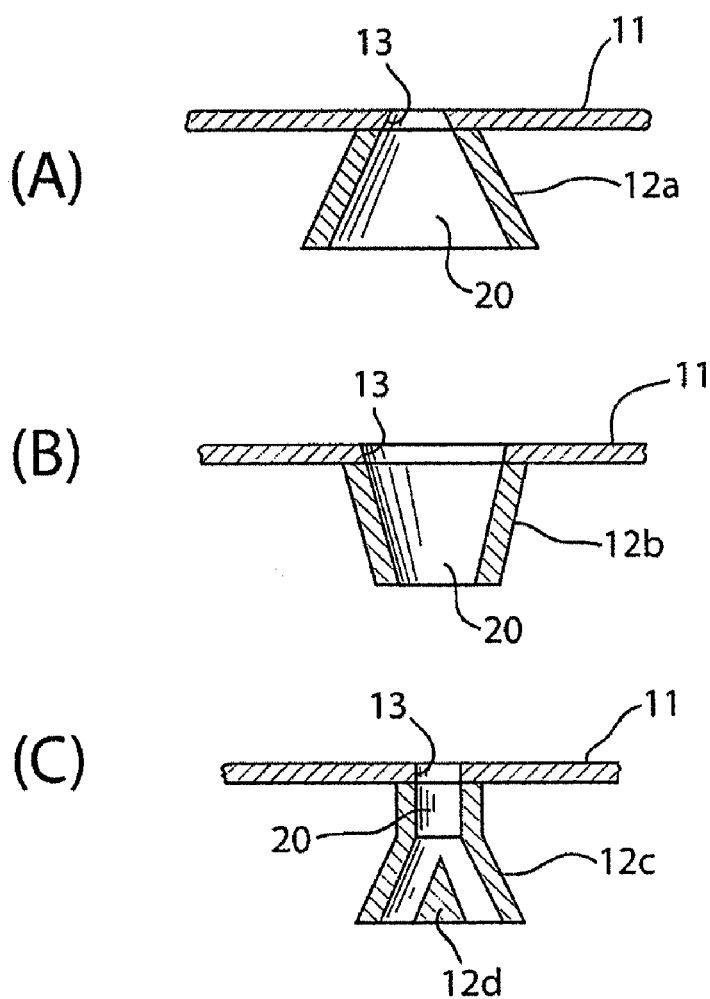
FIGS. 7(A) to 7(C) show vertical sectional views of different shapes of a tube portion applied to the liquid distribution unit of the present invention.

An introductory tube 12a shown in FIG. 7(A) has a truncated conical shape whose end being in contact with the opening of the sheet 11 of liquid impermeable material has a small diameter and which successively enlarges toward an end on a distant side.

An introductory tube 12b shown in FIG. 7(B) has a shape vertically reverse to that of the introductory tube 12a of FIG. 7(A). Furthermore, an introductory tube 12c shown in FIG. 7(C) has a cylindrical shape having an equal diameter down to a position corresponding to approximately the half of the length from an upper end, a lower connected portion has a truncated conical shape, a conical insert 12d is disposed in a truncated conical space, and the liquid passage in this portion is annular.

It is possible to apply introductory tubes having various shapes, but in many cases the shape of FIG. 7(B) is preferred because the shape has advantages that the tube is easily formed and there is little reverse flow of the liquid.

The length (H) of the introductory tube is an important factor for determining the capacity of the passage. The longer tube is preferred but becomes thick. It is therefore necessary to adequately select the length. The length (H) is preferably not less than 0.5 mm and not more than 10 mm, and further preferably 1.0 mm to 5 mm.

The liquid distribution unit of the present invention is attached to the absorbent article so as to cover all or part of the surface of the absorbent disposed closely to a wearer's skin (hereinafter referred to as the "upper surface"). In many absorbent articles, the upper surface of the absorbent is covered with a liquid permeable sheet (i.e., the top sheet) obtained by hydrophilic-treatment of a nonwoven fabric containing synthetic fibers such as PE, PP, PET which are major components. The liquid distribution unit of the present invention is preferably disposed on the surface sheet, that is, an outermost surface. When the top sheet is not disposed and the acquisition layer is disposed in the outermost surface, the unit is disposed on the acquisition layer. In the case of using an absorbent sheet composed of a substrate and super absorbent polymer particles, the substrate sometimes has a top sheet or acquisition effect. In this case, the liquid distribution unit is disposed so as to directly come in contact with the absorbent sheet. However, when the surface sheet is closely attached or bonded to the liquid distribution unit by an appropriate measure, and even when the unit is disposed right under the surface sheet, the unit is disposed substantially in the vicinity of the skin, and this is therefore included in the scope of the present invention.

The liquid distribution unit of the present invention has a function of controlling the distribution of body fluid, and therefore needs to be disposed in the vicinity of a body fluid discharge port, but the area, which can sufficiently cover the discharge port portion, is sufficient. It is unnecessary to cover all the large area of the absorbent member. When the absorbent member entirely covered with the surface sheet is assumed, the covering of the half (50%) of the surface sheet at maximum is sufficiently enough for the necessary area of the liquid distribution unit. Also considering from economy of the article, the area, which is not less than this size, is totally useless. However, the area needs to be about at least 3%, and a concretely necessary area of the absorbent article would be 10 $cm^2$ or more.

In this manner, since the liquid distribution unit needs to come in contact with the discharged body fluid as directly as possible, it is important to dispose the unit in the vicinity of the body fluid discharge port. Therefore, it is also necessary to change the disposed position in accordance with uses for men, women, adults, and children depending on the circumstances.

Table 1 shows a result of a test for measuring a change of an absorption speed with respect to an occupied area of the liquid distribution unit on the outermost surface. We adopted as the distribution unit an opening film (trade name "X-27373", thickness of 1184 μm) manufactured by Tredegar Co. 100 ml of a physiological salt solution was supplied via a nozzle having a nozzle diameter of 2 mm, and absorption time was measured to carry out the test. While a positional relation between the liquid distribution unit and absorbent member was set as shown in FIG. 9 described later, an experiment was carried out. It is seen from the result of Table 1 that a system not including the distribution unit requires 170 sec, while the absorption-time is reduced to about ⅕ or less in a system including the distribution unit. When the occupied area is not less than 20 cm² as the cover area of the liquid distribution unit, the absorption speed is seen to be hardly influenced. It is to be noted that a discharge speed of urine by a healthy baby or adult is 60 sec or less per 100 ml. When the absorbent article is considered, for the whole absorption ability, in terms of a retention amount (retained absorption amount), the article is generally designed to have a retained absorption amount of 300 ml or more. It is also important to reduce the absorption speed to 60 sec or less, preferably 40 sec or less per 100 ml.

This experiment result is a proof indicating that the distribution unit of the present invention is based on a physical mechanism which is different from the so-called acquisition effect. The degree of aquisition effect becomes nearly proportional to the occupied area.

TABLE 1

Occupied Area and Absorption Speed of Distribution Unit

|  | Control | Exp. 1 | Exp. 2 | Exp. 3 | Exp. 4 | Exp. 5 |
|---|---|---|---|---|---|---|
| Area of liquid distribution unit (cm²) | 0 | 10 | 20 | 40 | 100 | 350 |
| Occupying ratio in total surface area of absorbent member (%) | 0 | 2.9 | 5.7 | 11.4 | 35 | 100 |
| Absorption speed of 100 ml artificial urine (sec) | 170 | 35 | 28 | 30 | 29 | 30 |

Figure 8:
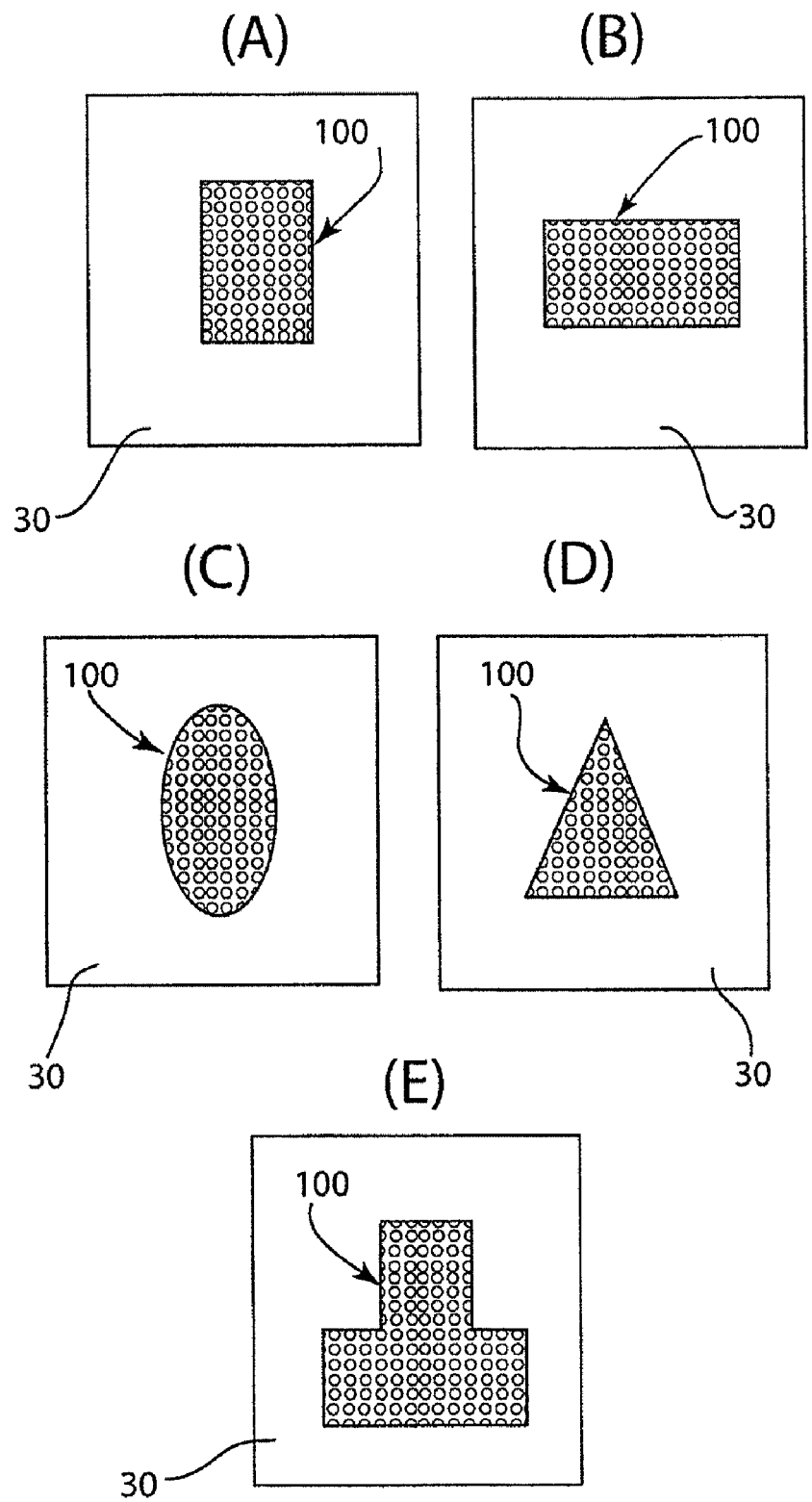
FIGS. 8 (A) to 8 (E) show plan views showing different modes of liquid distribution unit arrangement of the present invention to be combined with an absorbent member.

In the present invention, with the use of a liquid distribution unit having an area only covering only a part of the total surface of the surface sheet of the absorbent, its plane shape changes in accordance with a targeted capability, or various conditions of a use mode. Some shapes are shown in FIGS. 8(A) to 8(E). In these figures, reference numeral 30 denotes the absorbent member of the absorbent article, and the liquid distribution unit 100 of the present invention is disposed on the top sheet. The liquid distribution unit 100 has a vertically long rectangular shape in the example of FIG. 8(A), and has a laterally long rectangular shape in the example of FIG. 8(B). The liquid distribution unit 100 may have various shapes such as an elliptic shape as shown in FIG. 8(C), a triangular shape as shown in FIG. 8(D), and a convex shape as shown in FIG. 8(E).

The absorbent part of the absorbent article including the liquid distribution unit of the present invention basically includes the absorbent member, and the liquid distribution unit disposed on the absorbent member. The absorbent member may also include a usual structure constituted of a laminate material of super absorbent polymer particles and pulp, and a cover sheet with which the laminate material is covered, but preferably has a large content of super absorbent polymer particles. The absorbent member is preferably a pulp-less ultrathin absorbent sheet including a support sheet and an absorbent layer supported on the surface of the support sheet and containing the super absorbent polymer particles as a major component. The major component indicates an occupying state of 50% or more, preferably 60 to 90% of the total component weight involved in the absorption.

FIG. 9 shows the structure of an absorbent part in an absorbent article including an absorbent member 40 and liquid distribution unit 100. For the sake of simplicity, other accessory elements such as a back sheet and bonding unit are omitted. In this embodiment, in the absorbent member 40, there are disposed: a first absorbent sheet 43 including a liquid permeable support sheet 41 and strip-shaped absorption layers 42 disposed in parallel with one another on the lower surface of the support sheet; and a second absorbent sheet 46 which is disposed under the first absorbent sheet and which includes a layer of super absorbent polymer particles 45 on the lower surface of a support sheet 44. The absorbent member 40 includes a top sheet 47 disposed on the first absorbent sheet 43, and the liquid distribution unit 100 is disposed on the top sheet.

The liquid distribution unit 100 has an about 50 cm² rectangular shape whose area is largely smaller than an area of 300 cm² of the absorbent member 40, and is disposed substantially in a center part of the absorbent member 40 as shown in FIG. 8(A).

A test was carried out to compare an absorption capability of the absorbent article including the liquid distribution unit of the present invention as shown in FIG. 9 with that of three types of control samples. The result is shown in the following Table 2.

The structures of comparative samples are shown in FIGS. 10(A), 10(B), and 10(C). Sample No. 1 has a structure of FIG. 10(A) excluding the liquid distribution unit 100 from the absorbent article of the present invention; sample No. 2 includes a structure of FIG. 10(B) in which instead of the liquid distribution unit 100, an acquisition layer 110 formed of an air-laid nonwoven fabric is disposed between the top sheet 47 and absorbent member 40; and sample No. 3 includes a structure of FIG. 10(C) in which instead of the liquid distribution unit 100, an acquisition layer 120 formed of a thermal bond nonwoven fabric is disposed over the whole surface between the top sheet 47 and absorbent member 40.

TABLE 2

Comparison of Absorption Speeds

|  | Comparative sample No. 1 | | Comparative sample No. 2 | | Comparative sample No. 3 | | Present invention | | |
| --- | --- | --- | --- | --- | --- | --- | --- | --- | --- |
|  | First absorption | Second absorption | First absorption | Second absorption | First absorption | Second absorption | First absorption | Second absorption | Third absorption |
| Weights of liquid distribution unit or acquisition layer (g/cm$^2$) | — | — | 100 | 100 | 50 | 50 | 38 | 38 | 38 |
| Thickness of liquid distribution unit or acquisition layer (mm) | — | — | 1 | 1 | 0.6 | 0.6 | 1 | 1 | 1 |
| Thickness of absorbent member (mm) | 0.6 | 0.6 | 1.7 | 1.7 | 1.5 | 1.5 | 0.6 | 0.6 | .06 |
| Relative ratio of total thickness (%) (on basis of sample No. 3) | 40 | 40 | 113 | 113 | 100 (Standard) | 100 | 47 | 47 | 47 |
| Open area ratio (%) | — | — | — | — | — | — | 30 | 30 | 30 |
| Number of openings of liquid distribution unit (Openings/100 cm$^2$) | — | — | — | — | — | — | 1400 openings | 1400 openings | 1400 openings |
| Use area of liquid distribution unit (cm$^2$) | — | — | — | — | — | — | 50 | 50 | 50 |
| Absorption speed (Absorption time of 100 ml/sec) | 150 | 200 | 22 | 45 | 25 | 55 | 20 | 25 | 24 |
| Total absorption volume (ml) | 100 | 200 | 100 | 200 | 100 | 200 | 100 | 200 | 300 |

Although the liquid distribution unit of the present invention has a small installation area of 50 cm$^2$, it is seen that an absorption speed promotion effect equal to or more than that of the conventional acquisition material disposed over the entire surface is provided. Especially when the measurement is repeated twice, three times, the absorption speed largely drops in the conventional constitution. However, it is seen that with the use of the liquid distribution unit of the present invention, the speed is nearly the same even in the third absorption.

From the above test result, for the absorbent article including the liquid distribution unit of the present invention, while the absorption capability is enhanced, it is possible to largely reduce the entire thickness.

Figure 11:
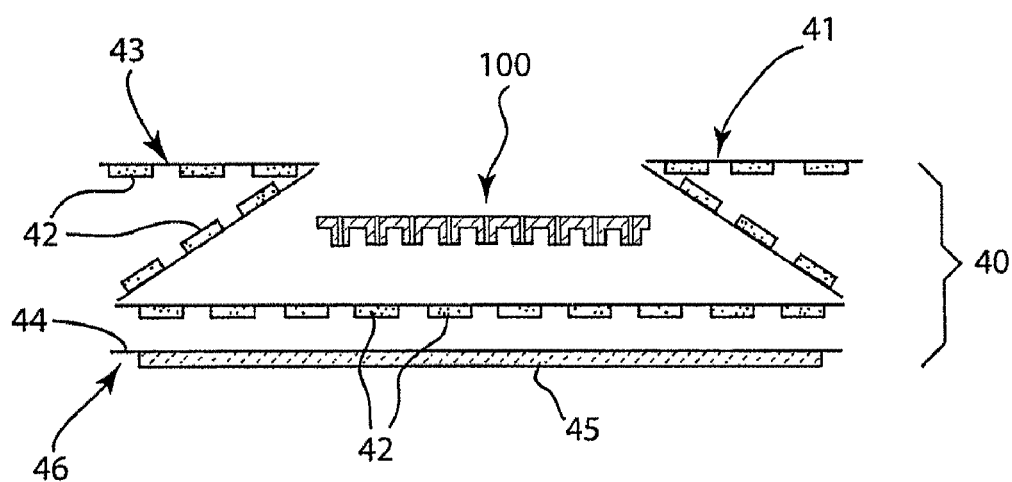
FIG. 11 is a vertical sectional view in a width direction, showing a constitution example of the absorbent member applied to the absorbent article of the present invention.

FIG. 11 is a vertical sectional view in a width direction showing a structure of the absorbent member 40 according to another example applied to the absorbent article of the present invention. For the sake of simplicity, the other accessory elements such as the back sheet and bonding unit of the absorbent article are omitted. In this example, a first absorbent sheet 43 includes a liquid permeable support sheet 41 and strip-shaped absorption layers 42 disposed in parallel with one another on the lower surface of the support sheet. Under this first absorbent sheet, a second absorbent sheet 46 is disposed including a layer of super absorbent polymer particles 45 disposed on the lower surface of the support sheet 44. The first absorbent sheet 43 is wider than the second absorbent sheet 46, and opposite side portions extending outwards from opposite edges of the second absorbent sheet 46 have a shape bent so as to have a Z-shaped transverse section. Moreover, the liquid distribution unit is disposed on the first absorbent sheet 43 in the middle part of the absorbent member 40 in the width direction.

In this constitution, the liquid supplied to the absorbent member 40 from above is branched/distributed by the liquid distribution unit 100, rapidly absorbed in a broad region in the surface of the first absorbent sheet 43, and further absorbed by the second absorbent sheet 46. The Z-shaped portion disposed on the side of the first absorbent sheet swells and rises in response to the absorption, and also has a function of a side bank for preventing sideward leak.

Figure 12:
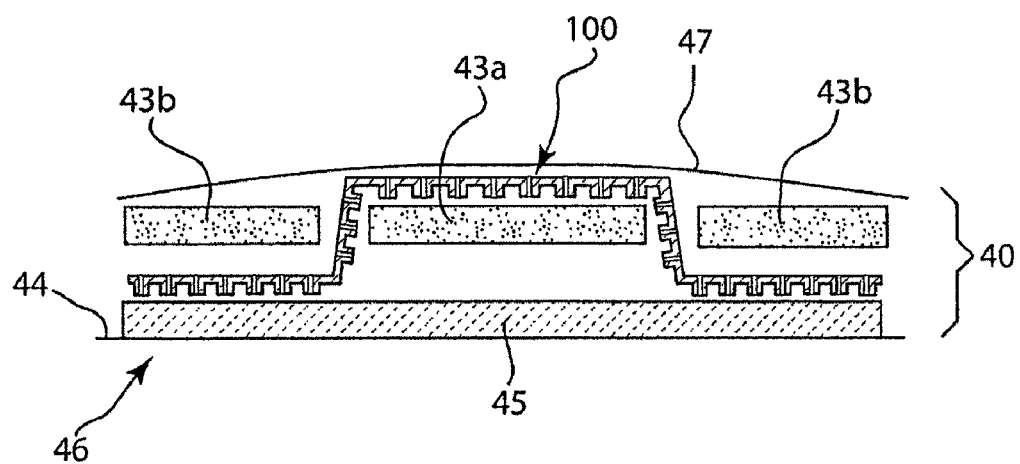
FIG. 12 is a vertical sectional view in a width direction, showing another constitution example of the absorbent member applied to the absorbent article of the present invention.

Furthermore, FIG. 12 shows a constitution in which the first absorbent sheet 43 includes an elongated middle portion 43a and a pair of elongated side portions 43b positioned on opposite sides of the middle portion. These portions are disposed on the second absorbent sheet 46, and further the liquid distribution unit 100 is combined with them. In this example, the liquid distribution unit 100 has a width substantially equal to that of the absorbent member 40, and is positioned on the first absorbent sheet 43a in the middle part of the width direction, but the opposite side portions of the unit extend between the first absorbent sheet 43a and the second absorbent sheets 43b and are disposed under the second absorbent sheets 43b. It is to be noted that, in this example, the top sheet 47 is disposed on the liquid distribution unit 100.

In this constitution, the liquid supplied to the absorbent member 40 from above is branched/distributed by the liquid distribution unit 100, rapidly absorbed in the newly whole region in the surface of the first absorbent sheet 43, further guided under the second absorbent sheets 43b by the liquid distribution unit 100, and further substantially simultaneously absorbed by the second absorbent sheet 46. Therefore, the unit is suitable especially for the absorbent structures such as diapers for children which deal with a large amount of liquid in a short time. It is to be noted that the lateral width of the distribution unit needs to be broadened, but the vertical width may be narrow.

Figure 13:
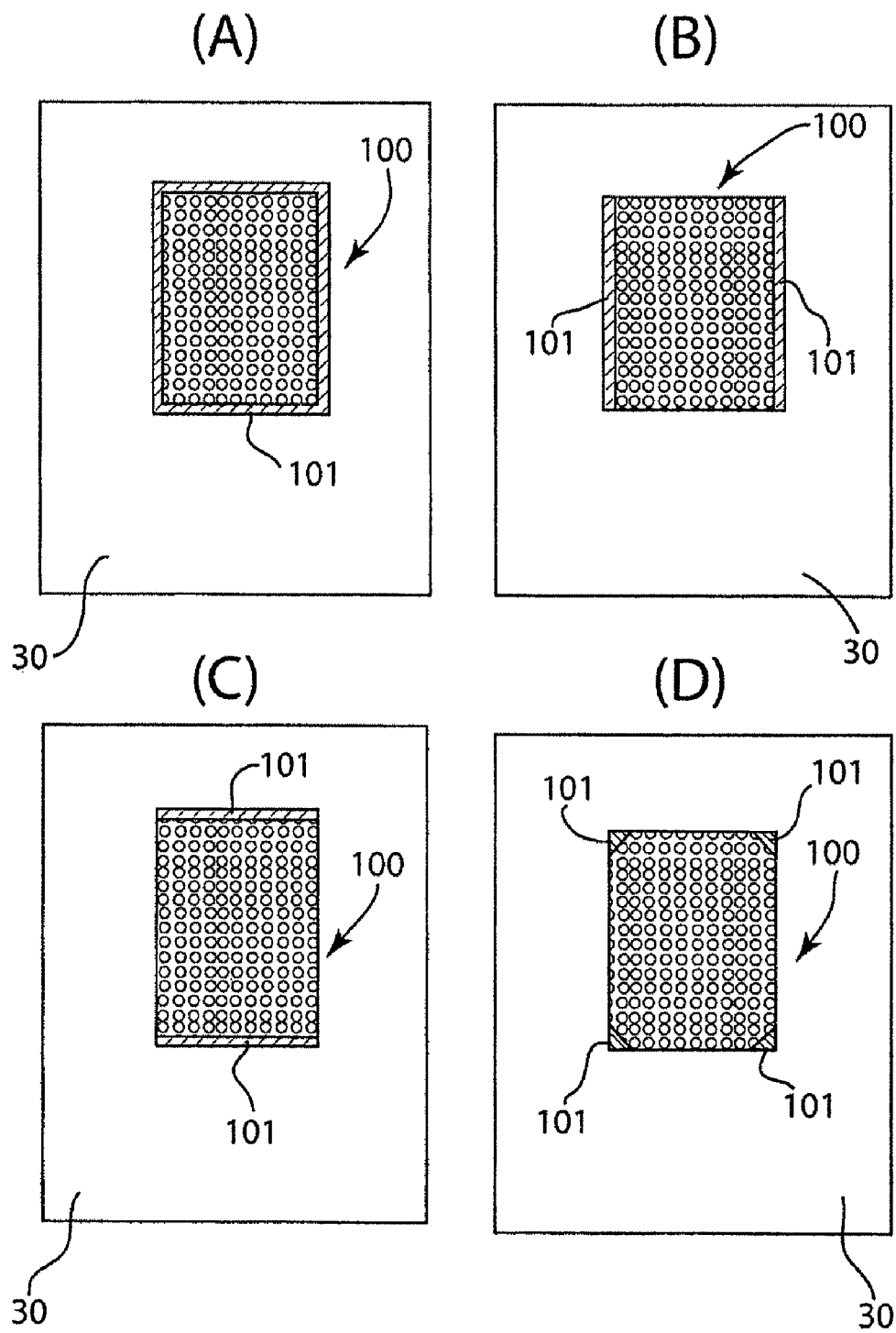

The mode in which the liquid distribution unit is bonded to the top sheet and/or directly to the absorbent is important because the division effect of the liquid is influenced. For example, the entire bonding of the unit by hot melt and the closing of distribution outlets have to be avoided. FIGS. 13(A), 13(B), 13(C), and 13(D) show examples in which the substantially rectangular liquid distribution unit 100 is bonded to the surface sheet of the absorbent member 30 in different portions. The unit is bonded by a bonding portion 101 over the entire four sides of the liquid distribution unit 100 in a sample S-1 as shown in FIG. 13(A), but the unit is bonded only in two long sides of the liquid distribution unit 100 in a sample S-2 as shown in FIG. 13(B), the unit is bonded in only two short sides of the liquid distribution unit 100 in a sample S-3 as shown in FIG. 13(C), and the unit is bonded in the bonding portions 101 only in four corner portions in a sample S-4 as shown in FIG. 13(D).

A test was carried out to check an influence of differences of these bonded states onto the absorption capability of the absorbent. The experiment was carried out by measurement of the absorption time of 100 ml of liquid with respect to each sample in a method similar to the above-described method, and the result is shown in Table 3.

TABLE 3

Fixing Method of Distribution Unit and Absorption Time of Liquid

| | Sample | | | |
|---|---|---|---|---|
| | S-1 | S-2 | S-3 | S-4 |
| Absorption speed (sec) | 58 | 42 | 38 | 30 |

For the sample S-1 bonded in all the four sides, even when the liquid was distributed, the distribution effect in the longitudinal and lateral directions remained only in the distribution unit area. Subsequently, the effect shifted inwards from the surface of the absorbent member 30. Therefore, the absorption required 58 seconds. For the S-4 partially fixed only in four corners, there were outlets in four directions, and therefore the liquid also diffused to the outside of the distribution unit in the longitudinal and lateral directions. The absorption ended in 30 seconds. Needless to say, when the liquid distribution unit was not used, the absorption required 150 sec to 180 sec. Therefore, even when the liquid distribution unit is bonded in all edges, the installation effect of the unit is large. However, attentions need to be paid to the change of the capability even with a fixing mode. Moreover, even when the liquid shift of the absorbent surface is controlled in the lower surface outlet of the liquid distribution unit, the surface diffusion state can be changed. That is, when the lower surface of the distribution unit is partially blocked by the liquid impermeable sheet, the absorption portion of the absorbent may be changed.

Figure 14:
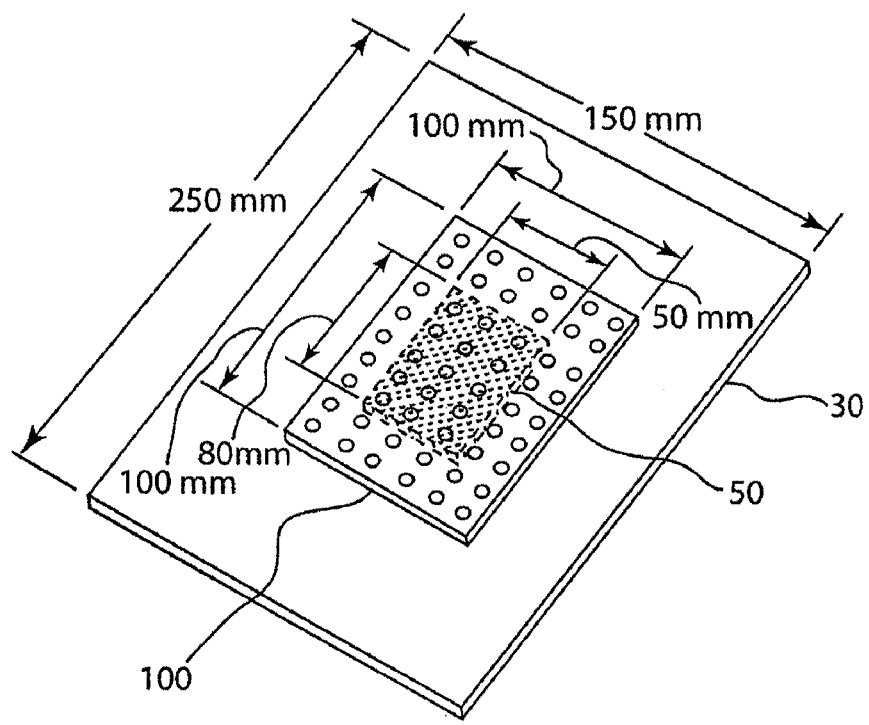
FIG. 14 is a perspective view showing another mode of the absorbent combined with the liquid distribution unit of the present invention.
Figure 15:
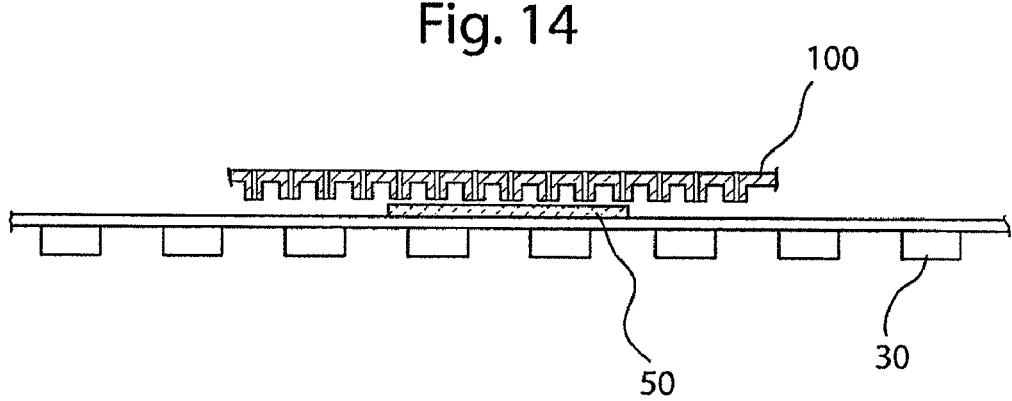
FIG. 15 is a vertical sectional view of FIG. 14.
Figure 16:
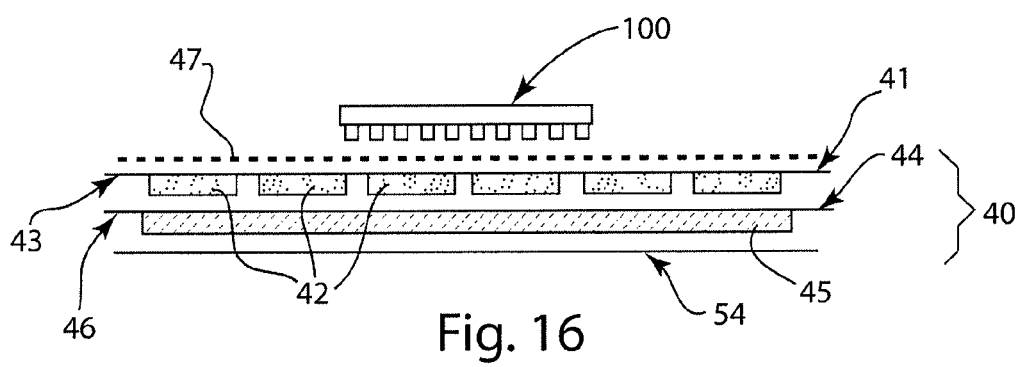
FIG. 16 shows a vertical sectional view schematically showing the parts of an absorbent article of the present invention.
Figure 17:
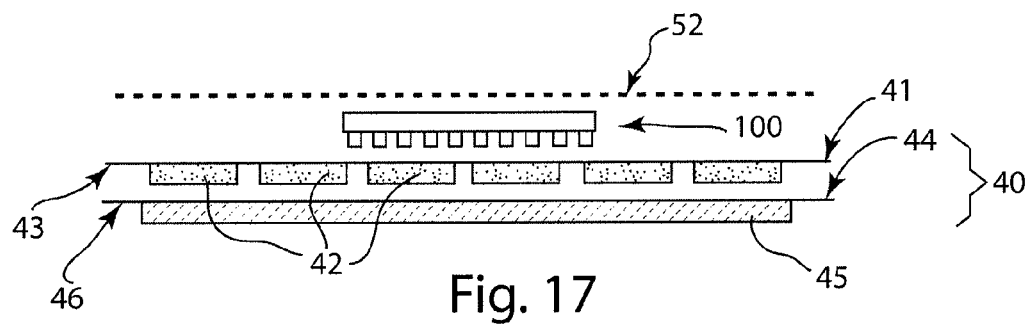
FIG. 17 shows a vertical sectional view schematically showing the parts of an absorbent article of the present invention.
Figure 18:
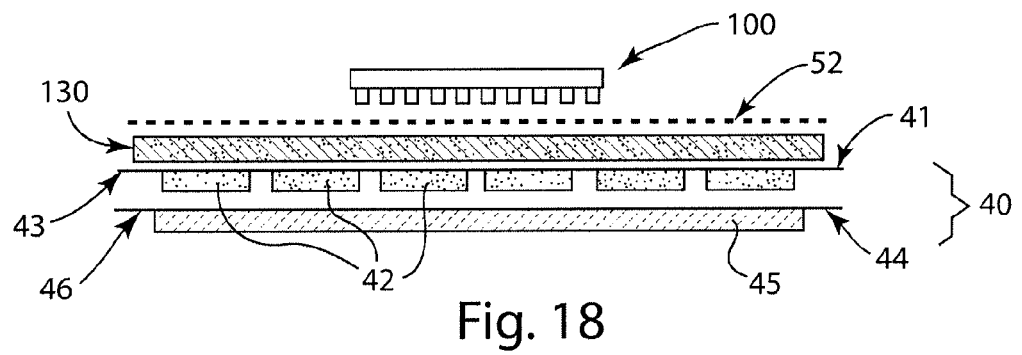
FIG. 18 shows a vertical sectional view schematically showing the parts of an absorbent article of the present invention.
Figure 19:
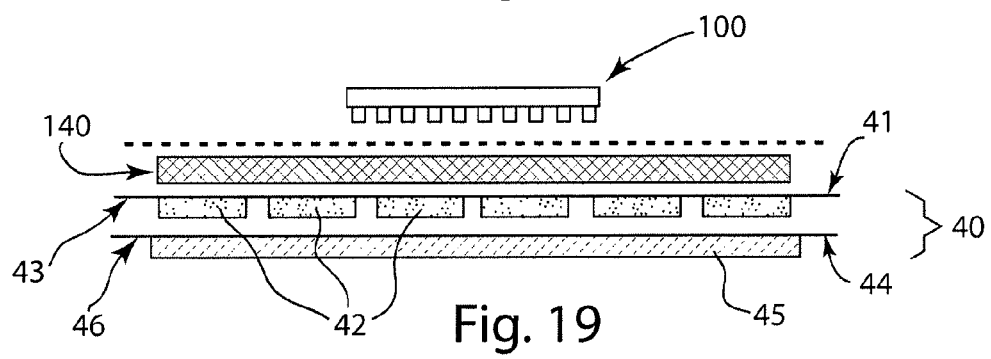
FIG. 19 shows a vertical sectional view schematically showing the parts of an absorbent article of the present invention.

FIG. 14 is a perspective view and FIG. 15 is a vertical section view. They show an example of the 100 mm×100 mm liquid distribution unit 100 laid on a 150 mm×250 mm absorbent member 30. In the unit, only a 50 mm×80 mm portion in the middle part is covered with a liquid impermeable sheet 50 formed of a PE film having a thickness of 30 μm, and the transfer of liquid into the absorbent member 30 is blocked in the portion. Accordingly, the liquid diffuses more broadly and speedily in the surface and is absorbed by the absorbent member 30 so that the whole absorbent is uniformly used.

In examples of FIGS. 14 and 15, a liquid impermeable sheet 50 of PE film is combined to the lower surface of a liquid distribution unit 100 by an adhesive, but may also be bonded on the side of an absorbent 30 or to the surface sheet (not shown). For the liquid impermeable sheet 50 for partially blocking the outlets of the liquid distribution unit, a film of as PE, PP, nylon, or PET, a water-resistant nonwoven fabric such as SMS, or a water-soluble PVA film, which temporarily has resistance to water but is melted away, is prepared in an appropriate area and shape in accordance with the area of the liquid distribution unit 100, and combined in an appropriate position. Accordingly, the transfer direction and state of the flow of the liquid which goes out can freely be controlled.

As described above, in the liquid distribution unit of the present invention, the body fluid irregularly discharged in the surface of the unit is divided and branched finely, along the surface of the surface sheet of the absorbent positioned below the unit by the mechanical distribution effect by a large number of liquid distribution passages. Accordingly, the liquid forms a controlled fine flow and rapidly spreads over the absorbent surface, only a part of the absorbent is prevented from locally absorbing/swelling, and the absorption capability of the absorbent can effectively be used.

Furthermore, in the absorbent article of the present invention including the above-described liquid distribution unit, the absorption capability of the used absorbent is fulfilled at the maximum to realize the enhancement of the capability of the absorbent article.

INDUSTRIAL APPLICABILITY

Liquid distribution units of the present invention improve absorption capabilities of absorbent articles such as diapers for infants and adults, sanitary items for women, and medical blood absorbents. Therefore these absorbent articles are produced in large amounts and are broadly used.

The invention claimed is:

1. A liquid distribution unit disposed in a position between an absorbent member and a wearer's body, the absorbent member including an absorbent containing super absorbent polymer particles as a major component, or the absorbent and a liquid permeable surface sheet between the absorbent and the liquid distribution unit,
    said liquid distribution unit comprising a sheet and a plurality of introductory tubes which extend toward an upper surface of said absorbent member, one first end of each of said plurality of introductory tubes having one opening and one second end of each of said plurality of introductory tubes having one or more openings,
    the sheet including a plurality of openings defined through material which is otherwise liquid impermeable, and the liquid passing through the plurality of openings,
    wherein each first end of said plurality of introductory tubes is connected to said sheet so that a center of each of the plurality of openings of said sheet is coincident with a center of the opening of each first end,
    each second end of said plurality of introductory tubes is in contact with the upper surface of said absorbent or the upper surface of said liquid permeable surface sheet, and
    said introductory tubes are adjacent to one another through an empty space.

2. The liquid distribution unit according to claim 1, wherein an open area ratio of the openings of said sheet is in a range of 10% to 90%, and the number of the openings of said sheet is at least 200 per 100 cm$^2$.

3. The liquid distribution unit according to claim 1, wherein each of said introductory tubes has a hollow truncated conical shape with an outlet diameter smaller than an inlet diameter and each second end has one opening, the inlet diameter being a diameter of the opening of each first end and the outlet diameter being a diameter of the opening of each second end.

4. The liquid distribution unit according to claim 1, wherein the length of each of said introductory tubes is in a range of 0.50 mm to 10 mm.

5. The liquid distribution unit according to claim 1, which is constituted of a thermoplastic film making a thickness in a range of 10 μm to 100 μm.

6. The liquid distribution unit according to claim 1, wherein the surface of the liquid distribution unit has a hydrophilic property.

7. An absorbent article comprising:
a liquid distribution unit;
an absorbent containing super absorbent polymer particles as a component disposed on an outer side of said liquid distribution unit with respect to a wearer's body in a wearing state; and
a liquid permeable surface sheet positioned on one of an inner side of said liquid distribution unit with respect to the wearer's body and an intermediate side between said liquid distribution unit and said absorbent, the intermediate side being the outer side of said liquid distribution unit,
wherein said liquid distribution unit comprises a sheet and a plurality of introductory tubes which extend toward an upper surface of said absorbent or said liquid permeable surface sheet, one first end of each of said plurality of introductory tubes having one opening and one second end of each of said plurality of introductory tubes having one or more openings,
the sheet including a plurality of openings defined through material which is otherwise liquid impermeable, and the liquid passing through the plurality of openings,
wherein each first end of said plurality of introductory tubes is connected to said sheet so that a center of each of the plurality of openings of said sheet is coincident with a center of the opening of each first end,
each second end of said plurality of introductory tubes is in contact with the upper surface of said absorbent when the liquid permeable surface sheet is positioned on the inner side of said liquid distribution unit and in contact with said liquid permeable surface sheet when the liquid permeable surface sheet is positioned on the outer side of said liquid distribution unit, and
said introductory tubes are adjacent to one another through an empty space.

8. The absorbent article according to claim 7, wherein the absorbent contains at least 50% by weight of the super absorbent polymer particles.

9. The absorbent article according to claim 7, wherein said liquid permeable surface sheet is a liquid permeable nonwoven fabric.

10. The absorbent article according to claim 7, wherein said liquid distribution unit has an area of at least 10 cm², the ratio of the area to a total area of the surface sheet is in a range of 3% to 50%.

11. The absorbent article according to claim 7 further comprising a liquid impermeable sheet disposed on the outer side of said liquid distribution unit,
wherein the liquid impermeable sheet is positioned between said liquid distribution unit and said absorbent when the liquid permeable surface sheet is positioned on the inner side of said liquid distribution unit, and the liquid impermeable sheet is positioned between said liquid distribution unit and the liquid permeable surface sheet when the liquid permeable surface sheet is positioned on the intermediate side between said liquid distribution unit and said absorbent, and
wherein area of said liquid impermeable sheet is smaller than that of said liquid distribution unit, and each second end of said plurality of introductory tubes is not in contact with the upper surface of said absorbent and said liquid permeable surface sheet in area of said liquid impermeable sheet.

12. The absorbent article according to claim 7, wherein the absorbent comprises an absorbent sheet including any of a nonwoven substrate, super absorbent polymer particles, and a microfibrillated cellulose.

13. The absorbent article according to claim 7, wherein the absorbent comprises an absorbent sheet selected from the group consisting of an air-laid wood pulp, super absorbent polymer particles, and a binder.

14. The absorbent article according to claim 12, wherein the liquid permeable surface sheet is positioned on the inner side of said liquid distribution unit, the absorbent sheet has such a shape that each of opposite side portions is bent to have a Z-shaped transverse section, and said liquid distribution unit is disposed on an upper surface of the absorbent sheet between the Z-shaped transverse sections of the opposite side portions.

15. An absorbent article comprising:
a liquid distribution unit;
an absorbent containing super absorbent polymer particles as a component disposed on an outer side of said liquid distribution unit with respect to a wearer's body in a wearing state; and
a liquid permeable surface sheet positioned on an inner side of said liquid distribution unit with respect to the wearer's body,
wherein said liquid distribution unit comprises a sheet and a plurality of introductory tubes which extend toward said absorbent, one first end of each of said plurality of introductory tubes having one opening and one second end of each of said plurality of introductory tubes having one or more openings,
the sheet including a plurality of openings defined through material which is otherwise liquid impermeable, and the liquid passing through the plurality of openings,
wherein each first end of said plurality of introductory tubes is connected to said sheet so that a center of each of the plurality of openings of said sheet is coincident with a center of the opening of each first end, and
said introductory tubes are adjacent to one another through an empty space,
wherein the absorbent comprises a plurality of absorbent sheets laminated upon one another, said plurality of absorbent sheets including a top sheet and a lower sheet located under said top sheet, and said liquid distribution unit has a first portion located on the top sheet, a second portion located on the lower sheet and a third portion for connecting the first portion to the second portion through the top sheet, and
wherein each second end of said plurality of introductory tubes at the first portion is contacted with an upper surface of said top sheet, and each second end of said plurality of introductory tubes at the second portion is contacted with an upper surface of said lower sheet.

* * * * *